United States Patent [19]
Goddard

[11] Patent Number: 5,602,094
[45] Date of Patent: Feb. 11, 1997

[54] TREATMENT OF TUMORS

[76] Inventor: David Goddard, 21 Gateway Dr., Great Neck, N.Y. 11021

[21] Appl. No.: 219,506

[22] Filed: Mar. 29, 1994

[51] Int. Cl.⁶ ............................................. A61K 38/09
[52] U.S. Cl. .................. 514/12; 514/13; 514/14; 514/15; 514/16; 514/17; 514/21
[58] Field of Search .................. 514/410, 12, 13, 514/14, 15, 16, 17, 21

[56] References Cited

U.S. PATENT DOCUMENTS

| | | | |
|---|---|---|---|
| 4,014,909 | 3/1977 | Torossion et al. | 260/397.45 |
| 5,527,775 | 6/1996 | Shorr et al. | 514/12 |

OTHER PUBLICATIONS

Biochem J. (1988)250: 125–32.

*Primary Examiner*—Brian M. Burn
*Attorney, Agent, or Firm*—Graham & James LLP

[57] ABSTRACT

Malignant gliomas are treated by modifying the eicosanoid biosynthetic pathway with reduction of the inhibitory effect of prostanoids on the cytotoxic activity of NK and LAK cells. Synthetic peptides, corresponding to shared sequences with phospholipase activating protein (PLAP), having the capacity to activate phospholipase $A_2$ ($PLA_2$), when administered in a delayed release delivery system, such as with agarose beads induce release of $PGE_2$, with significant tumor necrosis. A tumor model comprising an air pouch in the dorsum of rats is utilized for effective evaluation of the treatment, with tumor growth, treatment and evaluation of tumors grown therein.

5 Claims, No Drawings

5,602,094

TREATMENT OF TUMORS

FIELD OF THE INVENTION

This invention relates to treatment of mammals, including humans suffering from cancerous tumors, particularly malignant gliomas and other tumors of the central nervous system, and to tumor models for evaluating effectiveness of such treatments.

BACKGROUND OF THE INVENTION

In its ideal form, cancer therapy harnesses the innate immunity of the host mammal and specifically humans, suffering from cancerous cell growth, to combat malignancy. Spontaneously arising clones of malignant cells are normally eradicated through mechanisms involving mononuclear cells such as natural killers (NK) and lymphokine activated (LAK) cells. It has been suggested that the functionality of such cells is modulated by locally released inflammatory mediators, such as prostaglandins and leukotrienes, which are products of the eicosanoid biosynthetic pathway. Changes in the amount of locally released eicosanoids thus may alter the activity of NK/LAK cells.

Malignant gliomas (glial cells which have undergone malignant transformation) of the central nervous system are particularly difficult to treat effectively, since they frequently arise at surgically inaccessible sites in the central nervous system and they tend to be resistant to the standard cancer treatments of chemotherapy and radiation. Though malignant gliomas tend to be non-metastatic, they nevertheless cause death by pressure on vital centers as a consequence of their continued growth. Median survival, even in treated patients, is no more than about eighteen months.

Tumors of gliomas have been found to synthesize at least one polypeptide growth factor, basic fibroblast growth factor (bFGF), which stimulates production of eicosanoids, particularly $PGE_2$. This suggests that growth of gliomas, in vivo, is driven by bFGF and/or $PGE_2$.

As a start in determining a means for controlling eicosanoids it is initially known that eicosanoids are formed from arachidonic acid (AA) by one of two major pathways. Prostanoids, which tend to inhibit cytotoxic activity of NK and LAK cells, are formed as the result of hydrolysis of AA by the enzyme cyclooxygenase. These prostanoids include prostaglandins of the E and F series, prostacyclin, and thromboxanes. In the other major pathway, leukotrienes are formed by AA acted upon by lipoxygenases, particularly 5-lipoxygenase. Nearly all currently available non-steroidal antiinflammatory drugs operate through inhibition of cyclooxygenase activity.

A limiting step in the eicosanoid biosynthetic pathway is the generation of the intracellular AA. Formation of AA, which results in prostanoid production, occurs from the action of phospholipase $A_2$ ($PLA_2$). Recently, several natural activators of $PLA_2$ have been identified. Venoms, particularly of origin from bees and wasps, have been known to incite local tissue inflammation through generation of eicosanoids. The protein, mellitin, found in bee venom, has been discovered as having the capacity to enhance $PLA_2$ enzyme activity. Mellitin shows homology with phospholipase activating protein (PLAP) which has been isolated from the joint fluids of patients suffering from rheumatoid arthritis. Synthetic peptides corresponding to shared sequences of mellitin and PLAP have been recently shown to have the capacity to activate $PLA_2$ both in vitro and in vivo, with the induced release of $PGE_2$. Growth of gliomas is experimentally shown to be associated with the synthesis and release of $PGE_2$, $PGF_{1\alpha}$, $PGF_{2\alpha}$, and leukotriene $B_4$ ($LTB_4$).

SUMMARY OF THE INVENTION

Generally the present invention comprises the administration, such as by intravenous injection, to a patient in need thereof, of materials which have the capacity to enhance $PLA_2$ enzyme activity. These materials specifically include PLAP, synthetic peptides thereof, or other analogs thereof, and comprise shared sequences of mellitin with PLAP (hereinafter referred to collectively as "PLAP"), having the capacity to enhance $PLA_2$ enzyme activity. Such administration, when effected by sustained release delivery means, induces tumor necrosis in mammals including humans. Suitable doses over the for effective reduction of tumor growth are from 0.5 to about 2.0 mg/kg body weight/day, although the optimum dosage will be determined by the physician taking into account the age, weight and general health of the patient. Preferably, the sustained release form provides relatively uniform release of active substance. Doses may also be administered in several treatments over a period of time to achieve the overall requisite sustained delivery treatment, in lieu of a single delay release delivery administration.

The sustained release dosage treatment can be effected in various known forms. These include, for oral administration, placing the therapeutic material in a time disintegrating tablet or pellet coated with various thicknesses of known materials such as carnuba wax, cellulose esters and ethers, fats, keratin, gluten or various natural or synthetic esters. Tablets in which the selected agent is contained in a slowly dissolving core such as dehydrogenated castor oil or fatty acids can also be employed. Alternatively, the active material can be bound to an ion exchange resin such as a sulfuric acid type cation exchange resin.

A number of transdermal formulations can be used as the route of administration according to the present invention. Discrete dosage forms are prepared which, when applied to the skin, deliver the therapeutic agent through the skin at a controlled rate for systemic circulation. A transdermal system typically comprises an outer covering barrier, a drug reservoir which may have a rate of release controlling membrane, a contact adhesive applied to some or surface area at the skin interface and a protective layer which is removed before applying the adhesive to the skin. The drug reservoir is normally some type of polymer matrix such as a polyvinylpyrrolidone or a silicone polymer from which the drug is slowly released. A microporous membrane such as a polypropylene film may serve as a membrane to control the rate of release.

For intravenous administration, the most efficient system comprises PLAP, preferably bound within a delayed release delivery system such as one comprised of agarose beads. Such a system, effected by simple mixture of the PLAP and agarose beads, provides a demonstrated significant necrosis of tumor tissues, even of malignant gliomas, normally resistant to standard chemo- and radiation therapy treatments, within 72 hours after administration. With the tumor necrosis, the PLAP induces the exudation of $PGE_2$ and $PGF_{2\alpha}$ from the tumor. There is also evidence of tissues with mononuclear cells bearing an NK/LAK phenotype, with the exudation.

Agarose beads alone do not however provide such effect nor does PLAP in which amino acid substitutions result in loss of $PLA_2$ enzyme activating activity. Furthermore, simple non-sustained treatment with PLAP has not shown any significant tumor necrosis effect.

In order to test the effectiveness of the administration of the treatment, a tumor model has been developed and is within the purview of the present invention. The tumor model comprises formation of an air pouch in the subcutaneous tissues of the dorsum of a test animal, such as a rat, by the injection of sterile air therein. Generally about 20 cc is sufficient. Inflation of the formed pouch is maintained by re-injection of sterile air every other day until the pouch was ready to use for insertion therein of the tumor growth cells. The pouch has proven to be an ideal isolated site for tumor growth which occurs, with ready availability of tumor growth materials, despite isolation thereof from organs of the rat. This isolation thus provides a readily observable and treatable site for tumors without complicating attribution to other factors within the rat. Though similar pouches have been utilized as a method for observing the induction and progression of adjuvant polyarthritis ("A time course study of the changes that occur to the subcutaneous model of synovium following polyarthritogen"-by F. B. De Brito, A. R. Moore, D. G. Corry and D. A. Willoughby, Br. J. exp. Path., vol. 68, pp 559–567, 1987), they have not been used or suggested for use as a site for tumor growth, treatment and observation.

DETAILED DESCRIPTION OF THE INVENTION

The following discussion details formation of the glioma cells, formation of tumors therewith in rats, in accordance with the tumor model, the synthesis of the active PLAP peptide, treatment of the tumors, and analysis of the treated tumors. It is understood that the discussion is illustrative of the tumor treatment regimen of the present invention and that details contained therein are not to be construed as limitations on the present invention, particularly with respect to the nature of the tumors being treated. Tests were conducted with twelve rats treated and twelve rats as controls for each protocol described.

CULTURE OF GLIOMA CELLS:

Glioma cells were derived from a glioma induced in the Wister strain of rat and obtained from the American Type Culture collection (ATCC). The cell cultures from a tissue culture were grown to confluence in 75 cm$^2$ tissue culture flasks and detached therefrom by addition of trypsin/EDTA. The cell cultures were washed twice in fresh culture medium and re-suspended at a final concentration of $2 \times 10^6$ cells/ml.

AIR POUCH FORMATION FOR TUMOR GROWTH:

Air pouches were formed in female Wister rats (average age between 6–8 weeks, with an average weight of 180 gm). The air pouches were formed in the subcutaneous tissues on the dorsum of the rats by the injection of 20 cc of sterile air. Inflation of the pouches was maintained by re-injection of sterile air every other day until the pouches were ready to use on day 7.

FORMATION OF GLIOMAS:

Suspensions of cultured glioma cells (total number $1 \times 10^7$ cells) were injected into the air pouches. The air pouches were re-inflated with sterile air every other day for the first seven days after inoculation with tumor cells. By the seventh day, sufficient tumor growth had occurred and sterile air injection was stopped. By day 14, the tumors had reached sufficient size for experiments with the proposed treatment (with an average tumor weight of about 70 gm and overall individual rat weight of about 250 gm.).

SYNTHESIS OF PLAP PEPTIDE:

PLAP with phospholipase $A_2$-activation activity is described in "Tumour necrosis factor (cachectin) induces phospholipase $A_2$ activity and synthesis of a phospholipase $A_2$-activating protein in endothelial cells" by Mike A. Clark, Mann-Jy Chen, Stanley T. Crooke, and John S. Bomalaski (Biochem. J., vol. 250, pp 125–132, 1988). Synthetic PLAP peptides have been described in "Cloning of a phospholipase $A_2$-activating protein" by Mike A. Clark, Lynne E. Özgür, Theresa M. Conway, Janice Dispoto, Stanley T. Crooke and John S. Bomalski (Proc. Natl. Acad. Sci., vol. 88, pp. 5418–5422 June 1991), the disclosures thereof being included herein by reference thereto. PLAP is described in the former article as having been derived from mellitin (bee venom peptide) and the synthetic PLAP peptides with the phospholipase $A_2$-activating factor (with an amino acid sequence of PLAP having the greatest homology with mellitin (sequence 132) and which had been shown to activate $PLA_2$) as having been synthesized, from single stranded DNA, by t-butoxycarbonyl chemistry. The synthetic PLAP peptide, as described in the latter article, was used in the tests described below.

PREPARATION OF PLAP FOR INJECTION:

PLAP peptide, dissolved in sterile saline solution was bound, by simple overnight mixing, to agarose beads (Affigel Blue from BioRad, Melville, N.Y.) with a final concentration of 125 μg PLAP/ml of agarose beads. Prior to peptide binding, the beads were extensively washed in sterile deionized water to remove any endotoxin contamination.

Two groups of twelve rats were injected with the PLAP (500 μg/rat) and with agarose beads alone (as control), respectively. In order to ensure uniform distribution of the bound peptide, the total volumes (500 μg PLAP bound with 4 ml agarose beads and 4 ml of agarose beads alone) were increased to 10 ml by the addition of 6 ml sterile saline solution immediately prior to injection. Since tumor growth was characterized by formation of large effusions containing significant amounts of eicosanoids, the tumors were aspirated immediately prior to injection of PLAP peptide or agarose beads alone.

Seventy two hours after injection, the rats were euthenized by overexposure to $CO_2$ gas. The tumor effusions were aspirated. Estimates of cell numbers were made by Coulter counter and the fluids were stored at $-80°$ C. for eicosanoid assay. Tumors were removed through an incision made in the dorsum of the rats and weighed. Samples of tumor tissues were stored in formalin for routine histology and were snap-frozen in liquid nitrogen for immunocytochemistry.

HISTOLOGIC ANALYSIS OF THE TUMORS:

Formalin-fixed tumors were embedded, sectioned and reacted with hematoxylin and eosin according to standard methods and the sections were mounted and examined in an Olympus light microscope.

IMMUNOCYTOCHEMICAL ANALYSIS OF TUMORS:

Snap-frozen tissue samples were sectioned on a cryotome, fixed in acetone, blocked with levamisole, and then reacted with monoclonal antibodies to cell surface determinants expressed by mononuclear cells. After washing, tissue sections were reacted with biotin-labelled rat anti-mouse IgG monoclonal antibodies, alkaline phosphatase-labelled avidin-biotin complex (ABC; from Vecta, Burlinghame, Calif.) and color was developed by the addition of appropriate substrate. Sections were then mounted in Permount (Fisher Scientific) and read in the Olympus light microscope.

MEASUREMENTS OF EICOSANOIDS IN TUMOR EXUDATES:

Eicosanoid levels in exudates obtained from the tumors were determined using enzyme-lined immunoassay kits from Cayman Chemical Co. (Ann Arbor, Mich.).

GROWTH OF CULTURED GLIOMA CELLS IN THE AIR POUCH:

Appreciable tumor growth occurred in the air pouches within seven days of cell inoculation. By fourteen days, significant tumor growth had occurred and was accompanied by significant accumulations of exudate in the center of the tumors. Analysis of exudates obtained from tumors from treated and untreated rats identified eicosanoids from both the cyclooxygenase ($PGE_2$, $PGF_{1\alpha}$, $PGF_{2\alpha}$) and 5-lipoxygenase pathways ($LTB_4$ and $LTC_4$).

PLAP INDUCES NECROSIS IN GLIOMAS:

Injection of PLAP coupled to agarose beads which provided a sustained release of the peptide, caused significant necrosis in tumor tissues examined after 72 hours. These findings were accompanied by a reduction in tumor weight compared with control rats. These effects were not observed when agarose beads alone were injected into tumors. Moreover, injection of synthetic PLAP peptide without $PLA_2$ activating activity, did not cause tumor necrosis. The mechanism of tumor killing is therefore shown as being dependent on increased $PLA_2$ enzyme activity. To determine whether PLAP-induced tumor necrosis was accompanied by a change in the eicosanoid profile, eicosanoid levels were measured in the exudates harvested from the tumors. The amount of $PGE_2$ was greater in PLAP treated tumors compared with tumors injected with agarose beads. No changes were observed in the amounts of $LTB_4$ and $LTC_4$ in exudates from tumors treated with PLAP compared with those injected with agarose beads.

To determine whether PLAP-induced tumor necrosis was associated with specific cellular event, frozen sections of tumor tissues were reacted with MAbs directed at subpopulations of mononuclear cells. Injection of PLAP was associated with a mononuclear cell infiltrate, which comprises low number of ED1 positive cells (monocyte/macrophages) and high numbers of OX1 (cytotoxic T lymphocyte), NRK-1 positive (NK) cells. Since injection of agarose beads alone did not cause a similar mononuclear cell infiltrate, these data suggest the possibility that PLAP-induced tumor necrosis is mediated through enhanced NK/LAK cell activation.

It is understood that the above discussion and specific examples are illustrative of the present invention and that changes in protocol, materials, dosages and the like may be made without departing from the scope of the present invention as defined in the following claims.

What is claimed is:

1. A method for inducing necrosis of malignant glioma in mammals including humans, which comprises administering to such a mammal in need thereof, a sustained release composition comprising a malignant glioma necrosis inducing amount of phospholipase activating protein (PLAP) or a synthetic PLAP peptide, having phospholipase $A_2$ enzyme activating activity, in combination with a pharmaceutically acceptable carrier or diluent.

2. The method of claim 1, wherein said glioma is in the central nervous system of a human.

3. The method of claim 1, wherein said sustained release composition comprises the PLAP or PLAP peptide bound to agarose beads and the administration is by intravenous injection.

4. The method of claim 1, wherein said sustained release composition comprises a transdermal formulation and the administration is transdermal.

5. The method of claim 1, wherein said sustained release composition comprises a time disintegrating tablet and the administration is oral.

* * * * *